(12) United States Patent
Rakhorst et al.

(10) Patent No.: US 8,287,580 B2
(45) Date of Patent: Oct. 16, 2012

(54) METHOD AND A SYSTEM FOR PROLONGATION OF THE VIABILITY OF A DONOR ORGAN

(75) Inventors: Gerhard Rakhorst, Groningen (NL); Arjan Van Der Plaats, Groningen (NL); Rutger Jan Ploeg, Haren (NL)

(73) Assignee: Organ Assist B.V., Groningen (NL)

( * ) Notice: Subject to any disclaimer, the term of this patent is extended or adjusted under 35 U.S.C. 154(b) by 667 days.

(21) Appl. No.: 12/294,805

(22) PCT Filed: Mar. 28, 2006

(86) PCT No.: PCT/NL2006/000158
§ 371 (c)(1),
(2), (4) Date: Nov. 24, 2008

(87) PCT Pub. No.: WO2007/111495
PCT Pub. Date: Oct. 4, 2007

(65) Prior Publication Data
US 2010/0234928 A1 Sep. 16, 2010

(51) Int. Cl.
*A61F 7/00* (2006.01)
(52) U.S. Cl. ........................................ 607/105
(58) Field of Classification Search .......... 607/105, 607/104, 106, 113, 122
See application file for complete search history.

(56) References Cited

U.S. PATENT DOCUMENTS

| 4,473,637 A | 9/1984 | Guibert |
| 4,723,939 A | 2/1988 | Anaise |
| 5,110,721 A | 5/1992 | Anaise et al. |
| 5,505,701 A | 4/1996 | Anaya Fernandez de Lomana |
| 6,042,559 A | 3/2000 | Dobak, III |

FOREIGN PATENT DOCUMENTS

| DE | 43 24 637 A1 | 3/1995 |
| WO | 2004/026031 A2 | 4/2004 |

OTHER PUBLICATIONS

A.M. Scheule et al., "Emergency donor heart protection: application of the port access catheter technique using a pig heart transplantation model", Transplantation, vol. 77, No. 8, Apr. 27, 2004, pp. 1166-1171, XP002411400.
M.H. Booster, R.M.H. Wijnen, J.P.A.M. Vroemen, J.P. Van Hooff and G. Kootstra, "In situ preservation of kidneys from non-heart-beating donors—a proposal for a standardized protocol", Transplantation, vol. 56, No. 3, Sep. 1993, pp. 613-617, XP009075991.
M.A. Gok et al., "The effect of inadequate in situ perfusion in the non heart-beating donor", Transplant International, vol. 18, 2005, pp. 1142-1146, XP002411401.

*Primary Examiner* — Nicholas Lucchesi
*Assistant Examiner* — Brooke Matney
(74) *Attorney, Agent, or Firm* — Pearne & Gordon LLP

(57) ABSTRACT

For post-mortem prolongation of the viability of an organ (7, 8, 50, 51) in a donor body, a flow of a solution is introduced from outside the body between a pair of barriers (21, 22) and a return flow including previously introduced quantities of the solution is led to the outside of the body. During a flushing phase, the flow including blood flushed out of the organ (7, 8, 50, 51) is discharged to a drain. Subsequently during a recirculation phase, solution returned from the body is cooled and/or oxygenated and recirculated from outside the body back into the body between the barriers. A system for carrying out the method is also described.

20 Claims, 3 Drawing Sheets

METHOD AND A SYSTEM FOR PROLONGATION OF THE VIABILITY OF A DONOR ORGAN

FIELD AND BACKGROUND OF THE INVENTION

The invention relates to a method and a system for post-mortem prolongation of the viability of an organ in donor body.

In some organ donors, the so-called non-heart-beating donors (NHBD), cardiac arrest occurs before the organs can be retrieved. In other donors, the so called Brain Death or Heart Beating (BD or HB) donors, the circulatory system is kept functioning after death of the patient. After the circulatory system has stopped functioning, the organs will lack of oxygen. Moreover, at the moment of death, the organs are at body temperature and therefore in a high metabolic state with the associated high demand of oxygen and nutrients. The lack of oxygen in the still warm organs results in tissue damage. Tissue damage must be prevented, as it has a negative effect on the organ viability after transplantation. Reducing the warm ischemic time in organ donors would reduce tissue damage and result in maintaining a given level of viability for a longer period of time.

Accordingly, time is critical for organ donation. After the decease of a potential donor, generally approval for organ donation needs to be ascertained, before steps for organ extraction may be undertaken. Usual practice is to flush the organs to remove most of the blood from the organs and to cool the organs in order to prolong viability. After flushing, the organs are perfused with a preservation fluid to counteract further tissue damage during transport to the recipients.

Clinical death is determined by brain death or cardiac arrest. In case of death due to cardiac arrest, it is generally legally allowed to start flushing the organs, suited for donation after a period of 5 minutes of so-called "no-touch". Also after that period, in many cases, immediate explantation of organs is problematic or impossible, for instance because it would form an unacceptable disturbance for grieving relatives.

One known method for prolonging the viability of abdominal donor organs before explantation is in situ perfusion (ISP). Before the organs are taken out, a catheter carrying inflatable balloons is inserted to extend via the femoral artery into the abdominal aorta. Once in place, and after inflation of the balloons, the lower balloon cuts off the lower end of the aorta and the upper balloon cuts off the aorta at the level of the diaphragm. The lower and upper extremities, the torso and the head are thus excluded from perfusion. During perfusion, a perfusate flows out of the catheter between the two inflated balloons, and is forced to flow into the abdominal region, causing the organs to be flushed. The perfusate washes blood out of the organs to prevent clotting and cools the organs, thereby reducing metabolic requirements.

Another known method of prolonging the viability of abdominal organs before explantation from the donor body is extracorporeal membrane oxygenation (ECMO). Arterial and venous cannulae are placed following consent to donate, but prior to withdrawal of support. Circulation of blood is initiated immediately following declaration of death. Blood circulating via the cannulae is cooled and oxygenated before it flows back into the body. The circulation is maintained until the organs are taken out of the donor body. A blood pump drives the circulation.

Although an advantage of extracorporeal membrane oxygenation is, that oxygen is supplied to the organs, the viscosity of cold blood hampers oxygenation and the subsequent flushing of the organs forms an extra step that complicates the procedure and prolongs the time between death of the donor and implantation of the donated organ.

SUMMARY OF THE INVENTION

It is an object of the present invention to improve the viability of donor organs and in particular to counteract, or at least reduce the risk of warm ischemic trauma.

According to the invention, this object is achieved by providing a method according to claim 1. The invention can also be embodied in a system according to claim 10.

Because after in-situ flushing the organ in the donor body, oxygen is supplied and/or heat is withdrawn by recirculating an organ flushing and/or preservation liquid in-situ as well, the oxygenation and/or cooling of the organs can be started immediately after flushing irrespective of the circumstances and availability of surgical capacity for explantation of the organ. Accordingly, damage due to re-heating of the organ (and an associated increase in oxygen consumption) in the donor body that is generally still warm, after the organ has been cooled by flushing with a cold liquid, is effectively counteracted.

Compared with oxygenation by recirculating blood, the need of flushing after taking the organs out of the donor and the associated loss of time is avoided. When the organs have been taken out of the donor, the organs are immediately ready for transport or implantation.

Particular elaborations and embodiments of the invention are set forth in the dependent claims.

Further features, effects and details of the invention appear from the detailed description and the drawings.

DETAILED DESCRIPTION

Figure 1:
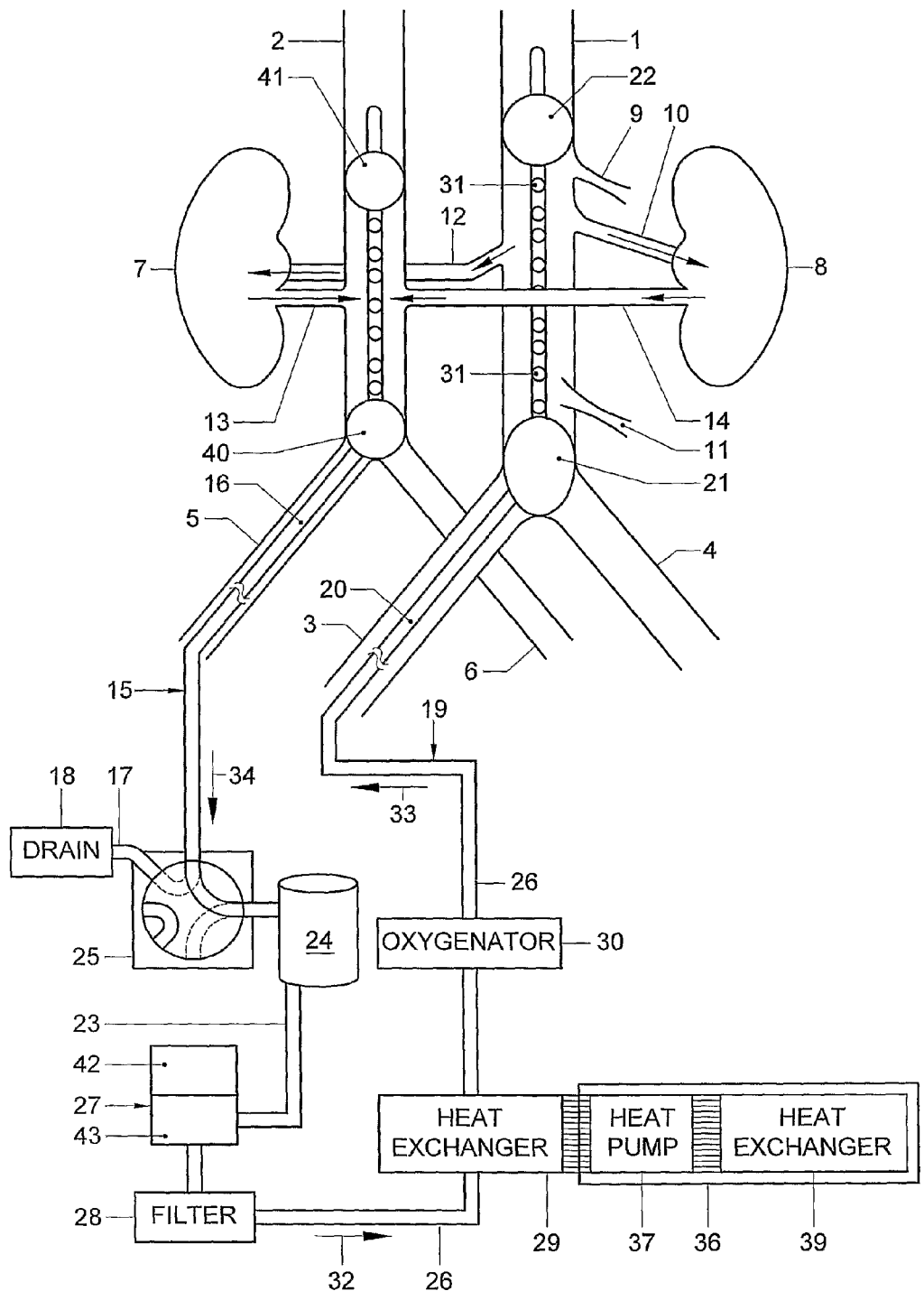
FIG. 1 is a schematic representation of portion of a donor body and of an example of a system according to the invention operatively connected to the donor body.

In FIG. 1, an aorta 1 branches out into the iliac and femoral arteries 3, 4. Femoral and iliac veins 5, 6 merge into a vena cava 2. The abdominal organs of the donor communicate with the aorta via arteries and communicate with the vena cava via veins. For the sake of simplicity, of the abdominal organs, only kidneys 7, 8 are shown. Furthermore, the renal arteries 10, 12, other arteries 9, 11 leading to other organs, of which transplantation may be intended as well, and the renal veins 13, 14 are shown as an illustrative example of portions of a donor body with which a system according to the invention may interact. Although the method and system according to the invention are illustrated by an example in which only preservation of the kidneys is shown, the invention may also be applied for the preservation of other organs, such as the liver or the lungs.

Hereinafter, first the example of an application of the invention illustrated by FIG. 1 is discussed. Preservation of the lungs is described later with reference to FIG. 4.

A distal end portion 16 of a return flow catheter 15 of an example of the system has been inserted into the vena cava 2 via femoral vein 5. A drain conduit 17 branches off from the return flow catheter 15 and leads to a drain collection reservoir 18. A distal end portion 20 of a solution-feeding catheter 19 has been inserted into the aorta 1 via the iliac artery 3. A first barrier 21 closes off the aorta 1 and the solution-feeding catheter 15 extends through a passage in the first barrier 21. The first barrier may also be positioned such that the iliac arteries are closed off. A second barrier 22 closes off the aorta 1 in a position spaced from the first barrier 21.

The catheters 15, 19 of the system according to the present example are double balloon triple lumen catheters (DBTL-catheter) containing three lumen. One relative large lumen, through which the solution flows, and two smaller lumen, each of them leading to a balloon. The barriers 21, 22 and similar barriers 40, 41 of the return catheter 15 are balloons inflatable by a pressurized fluid, flowing through the small lumen to the balloons.

Although, according to the present example, the barriers are mounted to the catheters via which the solution is fed and flows back, it is also possible to provide that one, some or all of the barriers, which may also be in a form other than that of a balloon, are not mounted to the catheters and applied in another manner, such as by means of one or more separate catheters that is retracted before the supply and return catheters are inserted.

A flushing solution supply conduit 23 is connected to a perfusion solution reservoir and communicates with the solution feeding catheter 19 via a valve 25 and a conduit 26 extending through a pump 27, a filter 28, a heat exchanger 29 and an oxygenator 30.

The pump 27 communicates with the solution feeding catheter 19 and, by operating the valve 25, may be caused to communicate alternatively with the flushing solution supply conduit 23 or with the return flow catheter 15, for pumping perfusion solution from either the flushing solution supply conduit 23 or the return catheter 15 to the solution feeding catheter 19.

For prolonging the viability of the organs 7, 8 after the death of the donor has been confirmed, the pump 27 is started with the valve 25 in a position indicated by dotted lines so that a flow of an organ flushing solution is pumped from outside the body into the aorta 1 via outflow openings 31 in the catheter 19 between the first barrier 21 and the second barrier 22. The first barrier 21 closes off the aorta 1 at the side of the arteries 9-12 remote from the heart and the second barrier 22 closes off the aorta 1 at the heart-side of the arteries 9-12. Arrows 32, 33 indicate the direction of the flow to the donor body.

A return flow in a direction indicated by arrow 34 is initially constituted by blood displaced out of the donor body by the flushing solution pumped into the donor body. As flushing progresses, an increasing proportion of the return flow is constituted by quantities of the flushing solution from the vena cava 2 to the outside of the body.

During flushing, the flow from the vena cava 2, including blood flushed out of the organs 14 is discharged via the drain conduit 17 to the drain reservoir 18.

Subsequently, the valve 25 is operated to start a recirculation phase during which the solution returned from the vena cava 2 is led to the pump 27, oxygenated in the oxygenator and recirculated from outside the body into the aorta 1 between the barriers 21, 22.

The initial washout of the donor organs provides rapid equilibration and effective cooling with preservation solution. Subsequently, organ viability prior to organ retrieval is further supported because the recirculation maintains the organs at an adequate temperature or even provides further cooling to the adequate temperature and oxygen is supplied to the organs. When the organs are taken out, the organs are ready for ex-vivo preservation, so that valuable time is gained and the need of manipulating organs after explantation is reduced. Moreover, although some preservation solutions in cooled condition have a higher viscosity than human blood at body temperature, the viscosity of preservation solutions at organ preservation temperatures of 0-4° C. is invariably lower than the viscosity of blood at such temperatures, so that a better organ perfusion can be achieved than with cooled blood. Also, by providing oxygen using a solution other than blood, the risk of red blood cell clotting during pumping is avoided.

The catheters via which the perfusate is introduced into the body may also be of a design suitable to be inserted via sub clavicle or carotid arteries instead of via the femoral arteries. The first (proximal) barrier then closes off the aorta at the heart side of the arteries and the second (distal) barrier then closes off aorta at the side of the arteries remote from the heart or closes off the iliac arteries. However, this would generally cause the presence of the organ preservation equipment to be more conspicuous, which may add to the distress of family of the deceased donor.

The flow of the solution introduced from outside the body into the aorta 1 may be a pulsatile or a non-pulsatile flow. To generate a plusatile flow, the pump 27 may be arranged for intermittently driving a liquid flow for generating a pulsatile flow.

The pump 27 may for instance be a centrifugal pump that is able to generate a continuous flow as well as a pulsatile flow, depending on how its motor is controlled, or a membrane pump that generates a pulsatile flow. The flow rate through the system is preferably in a range up to 4 l/min if all abdominal organs are to be flushed and preserved, or up to 500 ml/min if only the kidneys are to be flushed and preserved, at a pressure drop over the organs of up to 120 mmHg. Accordingly, in the present example, the pump 27 is preferably capable of maintaining a flow rate through the system of up to 4 l/min through all abdominal organs simultaneously, or of up to 500 ml/min for a pump to be used for flushing and preserving only the kidneys, in both cases, the pump is preferably capable of maintaining a pressure drop over the organs of up to 120 mmHg.

Although the oxygen supply during recirculation alone may be sufficient, cooling of the organs slows the organ metabolism and accordingly the oxygen need, which further helps avoiding warm ischemia. Cooling during recirculation is preferably achieved by cooling the solution returned from the vena cava 2 before recirculation into the aorta 1. During recirculation, the solution is cooled as it passes through the heat exchanger 29.

Depending on the circumstances lower flow rates than mentioned above can be preferable. To reduce the risk of damage to the organs, the flow rate through the organs is preferably caused or allowed to decrease as the organ cools down, taking into account stiffening due to hypothermic conditions and the decrease of the oxygen consumption as the temperature decreases.

The heat exchanger 29 is positioned upstream of the oxygenator 30. This is advantageous, because the oxygen solubility of cold water is higher than that of warm water.

Figure 2:
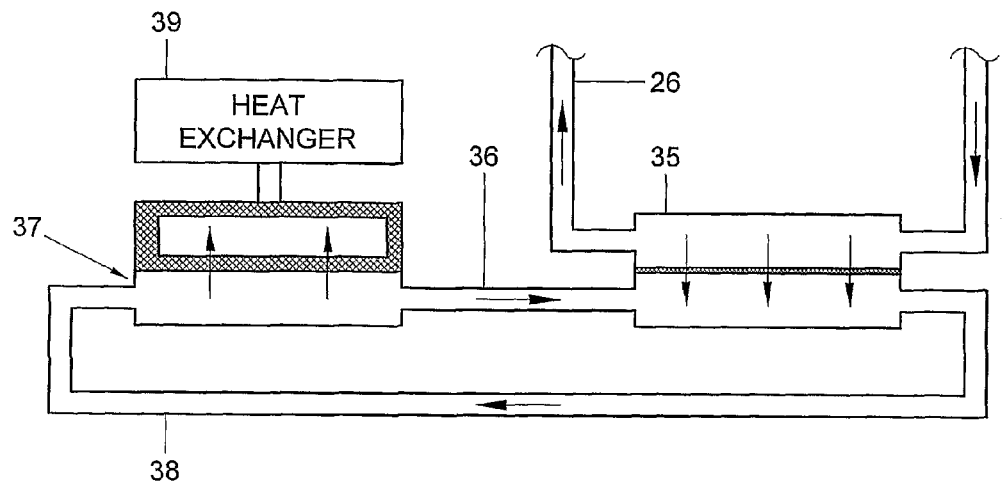
FIG. 2 is a schematic representation of a cooling portion of the system according to claim 1.

As is shown in FIG. 2, the heat exchanger 29 includes a conduit 35 for the solution to be cooled in heat exchanging contact with a cooling unit 36. The conduit 35 is disconnectable from the cooling unit, so that the conduit can be sterilized or disposed of after use while the cooling unit 36 can be re-used without any particular treatment. The cooling unit 36 includes a heat pump 37, a refrigerant circuit 38 and a heat exchanger 39 connected to the heat pump 37.

The flushing solution used for flushing the organs 14 and the preservation solution used during recirculation may be identical. However, for effectively flushing the organs, it is advantageous if the solution initially introduced into the aorta 1 before the start of the recirculation of the extracted and oxygenated solution is a solution having a lower viscosity than the solution introduced into the aorta 1 after the start of the recirculation of the extracted and oxygenated solution. This may for instance be effected by feeding the more viscous solution during a final portion of the flushing stage, such that at least a substantial portion of the less viscous solution in the system and the donor is flushed out and then continuing with recirculation of only or mainly the more viscous solution.

The supply of the more viscous solution may for instance be achieved by provisioning the reservoir 24 with such a solution during the flushing stage (for instance towards the end of the flushing stage) or by providing a second reservoir and switching to supplying solution from that second reservoir.

The flushing solution initially introduced into the aorta before the start of the recirculation may differ from the preservation solution introduced into the aorta after the start of the recirculation by a lower starch concentration.

The preservation solution may for instance contain hydroxyl ethyl starch (HES) or polyethylene-glycol (PEG) or other macromolecules to maintain osmolarity. Examples of solutions known in the art are UW (University of Wisconsin) machine preservation solution and Histidine-Tryptophan-Ketogluterate (HTK) solution.

For instance UW solution contains a small amount of oxygen as it is delivered in infusion bags. At 0-4° C., the solubility of oxygen is approximately the same as that of water (2.18 mmol/L at 0° C. under atmospheric pressure). Preferably, the solution is oxygenated to an oxygen saturation of at least 70-90% at a flow rate of at least 200 ml/min if a single organ is to be preserved and preferably at least 2 l/min if all abdominal organs are to be preserved. During recirculation, the pressure difference between the flow from outside the body into the aorta 1 between the barriers 21, 22 and the flow from the vena cava 2 to the outside of the body is preferably maintained at 20-60 mmHG.

The valve 25 is arranged for switching between a flushing operating condition in which the return flow catheter 15 communicates with the drain conduit 17 and a recirculation operating condition, in which the return flow catheter 15 communicates with the solution feeding catheter 19 for recirculating solution returned via the return flow catheter 15. An advantage of the using a valve or a plurality of valves for switching from flushing to recirculation is that all components of the system are attached to each other, before perfusion starts, so that the risk of contamination during perfusion is reduced. In stead, it is possible to disconnect the pump 27 from the solution feeding supply and connecting the pump to the return flow catheter 15 after flushing has been completed, but then the risk of contamination is higher.

The valve 25 is operable for switching from flushing to recirculation as a single operating step, which facilitates operation.

The filter 28 is preferably arranged for filtering out at least white blood cells and micro thrombi.

Figure 3:
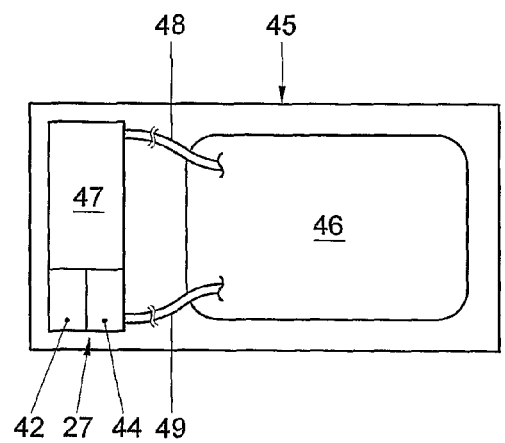
FIG. 3 is a schematic top plan view of an organ transport carrier containing a pump of the system according to the invention.

A system according to the invention may also include a box 45 for transporting an organ (see FIG. 3). The box 45 shown in FIG. 3 comprising a receptacle 46 for receiving the organ to be transplanted, a unit 47 for oxygenating the preservation solution and conduits 48, 49 for recirculating the preservation liquid through the organ. The pump 27 in the system shown in FIG. 1 is composed of a drive unit 42 and a liquid displacement unit 43 communicating with the conduits and releasably connected to the drive unit 42. In FIG. 3, the same drive unit is releasably connected to a liquid displacement unit 44 of the box 45 for driving the recirculation of the preservation liquid through the conduits 48, 49 of the box 45. By providing that at least the drive unit of the pump is releasably connectable to both the transport box 45 and the system for in-situ flushing and recirculation, a smaller number of drive units suffices for carrying out a method according to the invention. A system for carrying out one organ procurement may for instance be composed of one set of disposables for carrying out the flushing and recirculation, a transport box with disposable preservation unit, one reusable pump drive unit and one reusable cooling unit.

Since the pump comprises a drive unit 42 and a liquid displacement unit 43 communicating with the conduits 15, 19, 26, and the drive unit 42 is releasably connected or releasably connectable to the displacement unit 43, the drive unit can be transferred very easily from the system as shown in FIG. 1 to the transport box shown in FIG. 3 and back. In particular, this can be carried out without disconnecting conduits and the associated risk of contamination.

Figure 4:
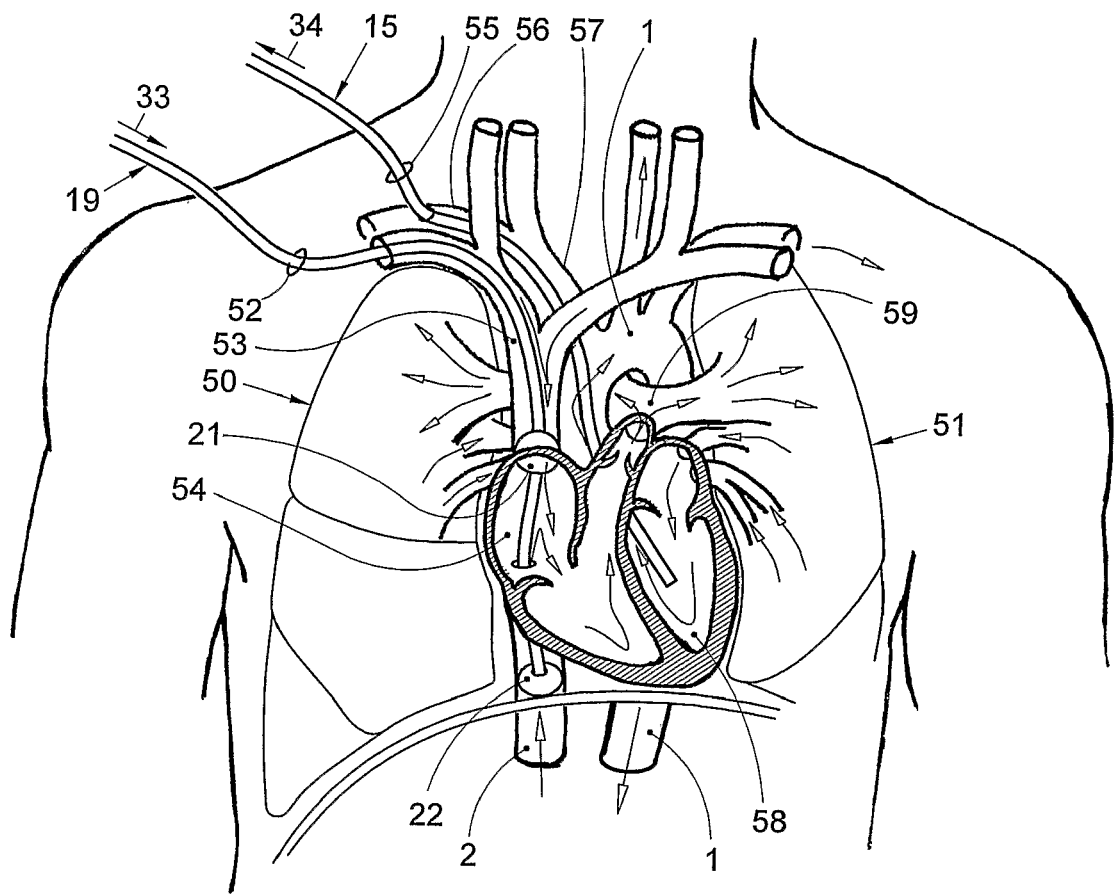
FIG. 4 is a schematic representation of portion of a donor body and of an example of a system according to the invention operatively connected to the donor body.

In FIG. 4, an example of application of the present invention to the procurement of lungs 50, 51 is shown. In FIG. 4, like parts are indicated by the same reference numerals as in FIG. 1. It is noted, however, that in practice it may be advantageous if dimensions of several parts of a system for flushing and recirculating through the lungs are different from dimensions of corresponding parts of a system for flushing and recirculating through abdominal organs.

The catheter 19 for supplying the flushing and preservation solutions is inserted into the donor body via an opening 52 and then led through the superior vena cava 53 into the right atrium 54 and positioned such that the outflow openings are located in the right atrium 54. The catheter 15 for leading the return flow out of the body is inserted into the body via an opening 55 and then led through the left sub-clavicle artery 56 and the brachiocephalic trunk 57 and the aorta 1 into the left ventricle 58 and positioned such that the intake opening is located in the left ventricle. The catheters may also be inserted such that the outflow openings of the supply catheter 19 are located in the right ventricle and/or such that the intake opening of the return catheter 15 is located in the aorta 1. In the present example, the first blood conduit is formed by the right atrium 54, the superior vena cava 53 and the inferior vena cava 2. The first barrier 21 closes off the superior vena cava 53 and the second barrier 22 closes off the inferior vena cava 2. In the present example, the barriers 21, 22 are located in the superior and inferior vena cava, but one of the barriers or both barriers may for instance also be located in the right atrium 54 to close off the respective vena cava at its end where it opens out into the right atrium 54.

During the recirculation phase, the solution returned from the left ventricle 58 or the aorta 1, is at least cooled. By flushing and subsequently recirculating via these catheters 15 and 19, a cold perfusion solution is administered to the lungs via the right atrium 54 and the right ventricle of the heart into the pulmonary artery 59 and the return flow is taken from the left ventricle 58 or the aorta 1. Accordingly the perfusion flow follows the natural flow pattern of blood through the pulmonary circuit.

Because it is the natural function of lungs to take in oxygen from inhaled air, oxygen is preferably supplied to the lungs 50, 51 by applying artificial respiration. In that situation, a system without an oxygenator can be used. However, additionally or alternatively, oxygenation of lungs to be transplanted may also be effected by oxygenating the recirculated solution.

The invention claimed is:

1. A method for prolongation of the viability of an organ in a deceased, donor body having a non-beating heart and blood conduits communicating with the organ to be transplanted, comprising:
   introducing, while the organ is in the donor body and while the blood conduits are in communication with the organ, a flow of a solution from outside the body into a first one of the blood conduits of the body in a position upstream of the organ and between a first barrier and a second barrier closing off the first blood conduit;
   leading a return flow including previously introduced quantities of the solution from a position in a second one of the blood conduits downstream of the organ to the outside of the body;
   during a flushing, non-recirculating phase, cooling the organ and discharging the return flow returned outside the body to a drain, the return flow including blood flushed out of the organ;
   subsequently, during a recirculation phase, at least oxygenating the solution returned from the body, and recirculating the returned solution from outside the body into the first blood conduit.

2. A method according to claim 1, wherein
   the organ is an abdominal organ;
   the first blood conduit is an aorta, an artery branches off from the aorta to the organ, a vein communicates with the organ and the second blood conduit is a vena cava into which the vein communicating with the organ opens out;
   the first barrier closes off the aorta at a side of the artery branching off to the organ remote from the heart or closes off the iliac and femoral arteries;
   the second barrier closes off the aorta between the artery branching off to the organ and the heart; and
   during the recirculation phase the solution returned from the vena cava, is at least oxygenated.

3. A method according to claim 1, wherein
   the organ is a lung;
   the first blood conduit includes a right atrium or a right ventricle and the second blood conduit includes a left ventricle or the aorta;
   the first barrier closes off the superior vena cava;
   the second barrier closes off the inferior vena cava; and
   during the recirculation phase, the solution returned from the left ventricle or the aorta, is at least cooled.

4. A method according to claim 1, wherein the solution initially introduced before the start of the recirculation is a solution having a lower viscosity than the solution introduced during the recirculation.

5. A method according to claim 4, wherein the solution initially introduced before the start of the recirculation is a solution having a lower starch concentration than the solution introduced during the recirculation.

6. A method according to claim 1, wherein the oxygenation and recirculation of the extracted and oxygenated solution is started by operating a valve structure.

7. A method according to claim 1, wherein the flow including the extracted and oxygenated solution that is recirculated is maintained at a flow rate of at least 200 ml/min.

8. A method according to claim 1, wherein a pressure difference between the flow from outside the body into an area between said barriers and the flow to the outside of the body of at least 60 mmHG is maintained during recirculation.

9. A method according to claim 1, further comprising filtering at least white blood cells and thrombi out of the solution before re-introduction of the solution into the body.

10. A method according to claim 1, wherein, during the recirculation phase, the solution returned from the body is cooled before recirculation of the returned solution from outside the body into the first blood conduit.

11. A method according to claim 1, wherein, during the recirculation phase, the recirculated solution comprises organ preservation liquid used during further preservation of the organ after explantation.

12. A system for prolongation of the viability of an organ while the organ is in a donor body, comprising:
   a solution-feeding catheter for introduction into a first blood conduit of a human body upstream of the organ while the organ is in the donor body, the solution-feeding catheter having an outflow opening;
   a return flow catheter for introduction into a second blood conduit of a human body downstream of the organ while the organ is in the donor body;
   a drain conduit branching off from the return flow catheter;
   a first barrier for closing off the first blood conduit on one side of the outflow opening and a second barrier for closing off the first blood conduit on an opposite side of the outflow opening;
   a flushing solution supply conduit communicating with the solution-feeding catheter;
   a pump communicating with the solution-feeding catheter and, in a flushing, non-recirculating operating condition, with a flushing solution reservoir and the drain conduit for discharging the return flow returned outside the body to a drain, and, in a recirculation operating condition, with the return flow catheter for recirculating solution returned via the return flow catheter; and
   at least an oxygenator which, in the recirculation operating condition communicates with the return flow catheter, the pump and the solution-feeding catheter for at least oxygenating the solution in a flow pumped from the return catheter into the solution-feeding catheter.

13. A system according to claim 12, comprising an oxygenator communicating with the return flow catheter for oxygenating the solution before recirculation into the body.

14. A system according to claim 12, comprising a heat exchanger communicating with the return flow catheter for cooling the solution before recirculation into the body.

15. A system according to claim 14, wherein the heat exchanger includes a conduit for the solution to be cooled and a cooling unit in heat exchanging contact with said conduit, and wherein the conduit is disconnectable from the cooling unit.

16. A system according to claim 12, further comprising at least one valve communicating with the solution-feeding catheter, the return flow catheter, the drain conduit and the flushing solution supply conduit, the valve being arranged for switching between a flushing operating condition in which the return flow catheter communicates with the drain conduit and a recirculation operating condition, in which the return flow catheter communicates with the solution feeding catheter for recirculating solution returned via the return flow catheter.

17. A system according to claim 16, wherein said at least one valve is operable for closing-off communication with the drain conduit and bringing the return flow catheter in communication with the solution feeding catheter, as a single operating step.

18. A system according to claim 12, further comprising, in a conduit interconnecting the return flow catheter and the solution-feeding catheter, a filter for filtering out white blood cells and thrombi.

19. A system according to claim 12, further comprising a container for transporting an organ, the container comprising conduits for recirculating a preservation liquid through the organ in the container, wherein at least a drive unit of the pump is connected or connectable to the container for driving the recirculation of the preservation liquid through the conduits.

20. A system according to claim 19, wherein the pump comprises a drive unit and a liquid displacement unit communicating with said conduits of said container, the drive unit being releasably connected or releasably connectable to the displacement unit.

* * * * *